United States Patent [19]

Oldendorf

[11] 4,174,635
[45] Nov. 20, 1979

[54] METHOD AND APPARATUS FOR ULTRA SOUND IMAGING UTILIZING RAYLEIGH BACKSCATTER

[76] Inventor: William H. Oldendorf, 2805 Angelo Dr., Los Angeles, Calif. 90024

[21] Appl. No.: 911,446

[22] Filed: Jun. 1, 1978

[51] Int. Cl.² ............................................. G01N 29/04
[52] U.S. Cl. ...................................................... 73/606
[58] Field of Search ................. 73/606, 627, 629, 620; 128/2 V

[56] References Cited

U.S. PATENT DOCUMENTS 4,078,435  3/1978  Kossoff et al. ........................ 128/2 V Primary Examiner—Anthony V. Ciarlante
Attorney, Agent, or Firm—Brown & Martin

[57] ABSTRACT

A diagnostic method and apparatus for ultrasound imaging utilizes Rayleigh backscatter of ultrasound waves directed to an object for creating an image of the object. The apparatus includes an ultrasonic generator for generating a pair of waves of slightly different frequencies which are directed through the object and, after their individual detection upon return from the interior of the object, the two signals representing the two frequencies are differentially amplified in order to emphasize the scattered waves returned from various regions of the object and minimize specular reflections, thereby characterizing the acoustical scattering properties of the interior of the object based upon regional scattering properties.

18 Claims, 11 Drawing Figures

METHOD AND APPARATUS FOR ULTRA SOUND IMAGING UTILIZING RAYLEIGH BACKSCATTER

BACKGROUND OF THE INVENTION

The present invention relates to ultrasound imaging and pertains particularly to the use of scattered ultrasound instead of specular ultrasound reflection for producing an image of the object.

The use of ultrasonic waves for detecting changes in density and the like in optically opaque bodies have been known for some time. Recent developments in ultrasound imaging have resulted in methods and apparatus for diagnostic investigation which has in many instances replaced traditional X-ray techniques. Ultrasound imaging has many advantages over radiography. Among these advantages are the ability to define soft tissues within the body. Other advantages include the lack of noticeable side effects. At energy levels used in medical diagnosis, ultrasound is believed to be completely harmless as opposed to the harmful effects of ionizing radiation which are well-known and accumulate with each additional exposure.

Ultrasound as presently employed utilizes predominantly the type of re-radiation from the interior of the examined object which is termed specular reflection. Specular reflection is a form of radiative return which obeys the law of reflection which states that the angle of incidence equals the angle of reflection.

Specular reflection as utilized in current ultrasound imaging devices exhibits certain specific properties. These include the fact that it follows the laws of reflection and is anisotropic in its propagation, that is, it is directional. Specular reflection is also independent of wavelength and frequency. The signals are typically strong and easily measured.

These are certain drawbacks, however, to the use of specular reflection in gaining information about an object. The main drawback is that, in order to obtain adequate information, it is necessary to scan an object from many different angles and positions. This imposes certain restrictions upon ultrasound in that it takes several minutes to produce a useful image using a perpherally moving scanning technique. It is necessary to either rotate the object or to move the equipment around the object to produce a coherent image. Overlying obstructions to the acoustical path, such as bone or gas, may seriously obscure the desired internal structure or region.

The present invention overcomes most of the drawbacks inherent in the prior art techniques of ultrasound imaging. The present invention is based on the exploitation of a certain aspect of re-radiated sound waves, Rayleigh scattering. Such scattering is re-radiation that does not obey laws of reflection in which the angle of incidence equals the angle of reflection.

When the size of the object is very small in relation to the wavelength of the incident wave, the scattered wave front exhibits several relevant properties. These are: (1) the scattered wave front propagates equally in all directions. This propagation is said to be isotropic. (2) The amplitude of the scattered wave front varies inversely with the fourth power of the wave length of the incident wave. A simplistic expression of this concept can be expressed by the formula $a = k(d/L)$, where "a" is the amplitude of the scattered wave front, "d" is the relevant dimension of the scattering object, "L" equals the wavelength of the incident wave front, and "k" is a constant specific to each experimental arrangement.

It is desirable to provide some method and apparatus that overcomes limitations inherent in current ultrasound imaging techniques. The present invention presents such a method and apparatus.

SUMMARY AND OBJECTS OF THE INVENTION

The primary objective of the present invention is to provide means for overcoming the above problems of the prior art by providing an ultrasound apparatus capable of producing a complete image of an object from a single external scanning point.

A further objective of the present invention is to provide an improved method and apparatus for ultrasound imaging utilizing Rayleigh backscatter.

In accordance with the primary aspect of the present invention an ultrasound imaging apparatus comprises of dual ultrasound generating means capable of generating dual ultrasound waves which can be differentially amplified to minimize specular reflections and maximize backscatter waves from the object with means for receiving and displaying an image defined by the scattered waves.

BRIEF DESCRIPTION OF THE DRAWINGS

The above and other objects and advantages of the present invention will become apparent from the following description when read in conjunction with the drawings, wherein.

DETAILED DESCRIPTION OF A PREFERRED EMBODIMENT

The present invention is based upon the use of certain characteristics inherent in scattered ultrasound waves. By utilizing these characteristics, a system is designed which is capable of seeing the distribution of scattering cross-section of tissue structure within a human body that specular reflection is inherently unable to detect. Another possible embodiment of the present invention would allow display of a geologic cross-section of the Earth's internal structure by defining regional scattering properties.

In summary, the present invention will concentrate on medical applications of enhanced Rayleigh backscatter imaging rather than specular reflection to derive the information necessary to form an image. This type of scattering is named after Baron John Rayleigh who first described the phenomenon in the mid eighteen hundreds.

Basically Rayleigh backscatter refers to a phenomenon wherein the amplitude of scattering of a wave front is dependent upon the relationship between the wavelength of the incident wave and the reflecting object's size. With this in mind, information may be obtained which will yield an image which represents the size and configuration of the reflecting object to a very high degree of accuracy.

Figure 1:
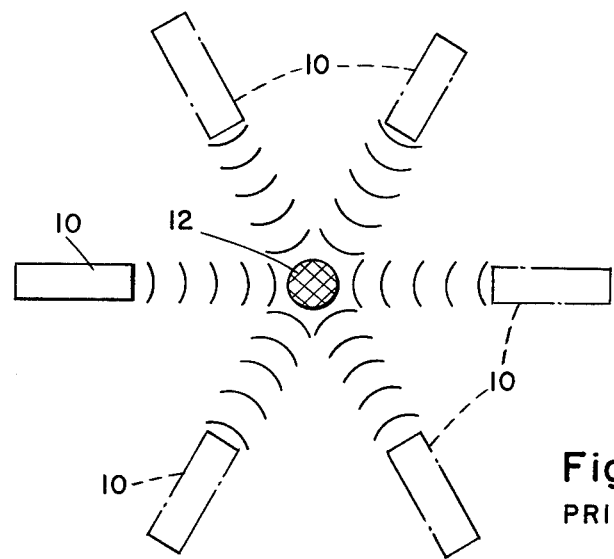
FIG. 1 is a schematic illustration of the prior art method.

As best illustrated in FIG. 1, the prior art approach to the scanning of an object in development of an image consists of a sound generator or transducer, designated generally by the numeral 10, which directs a ultrasonic wave front into a body such as the human body for detecting the image of a reflecting object 12. In order to obtain sufficient information to develop an image of the object 2 it is necessary to move the sound transducer to various positions, such as shown in phantom in FIG. 1. The angles of incident of the wave front require different positioning such as illustrated. The specular waves reflected off of the object 12 are picked up by a suitable instrument (e.g. the same transducer) and the information utilized to develop an image of the object 12. Because of the reflective characteristics of the specular waves of the object 12 it is necessary to scan the object from multiple positions around it. This is time consuming and in many instances, may be inconvenient. Because of the reflective nature of specular waves, the positioning of the ultrasound generator and the ultrasound pick up device are critical with respect to determining the characteristics of the body.

Figure 2:
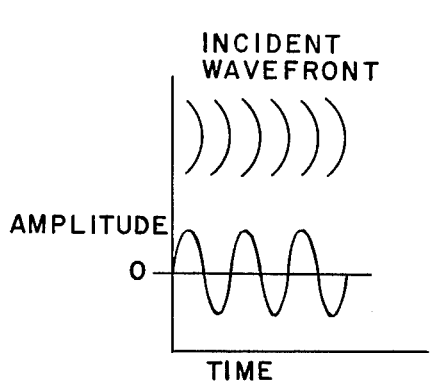
FIG. 2 is a graphic illustration of an incident wave front showing proportional amplitude.
Figure 3:
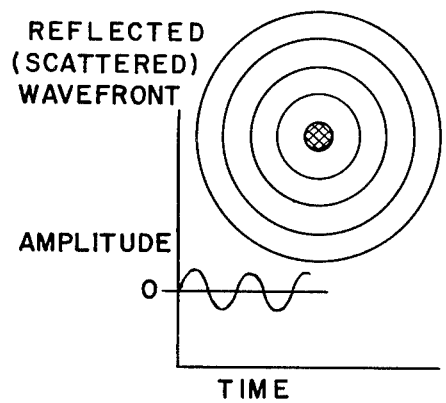
FIG. 3 is a graphic illustration of a reflected wave front showing amplitude for a given frequency.

The incident wave fronut will have a given amplitude for a given frequency of wave and the reflected wave front will have a similar amplitude. This is best illustrated in FIG. 2. Comparing this to the scattered wave front as illustrated in FIG. 3 for the same wavelength, it is seen that the amplitude of the scattered waves will be considerably less for the same wavelength or frequency. An important characteristic, however, of the scattered wave front is that as noted in FIG. 3, the waves will radiate outward equally in all directions from the object. Another important feature, as previously mentioned, is that the amplitude of the wave front will vary in accordance with the size of the body with respect to the wavelength. Therefore the wavelength can be matched to the body size of the reflecting object to provide optimum amplitude of the scattered wave front. Backscattered waves are also distributed relatively evenly over time.

Figure 4:
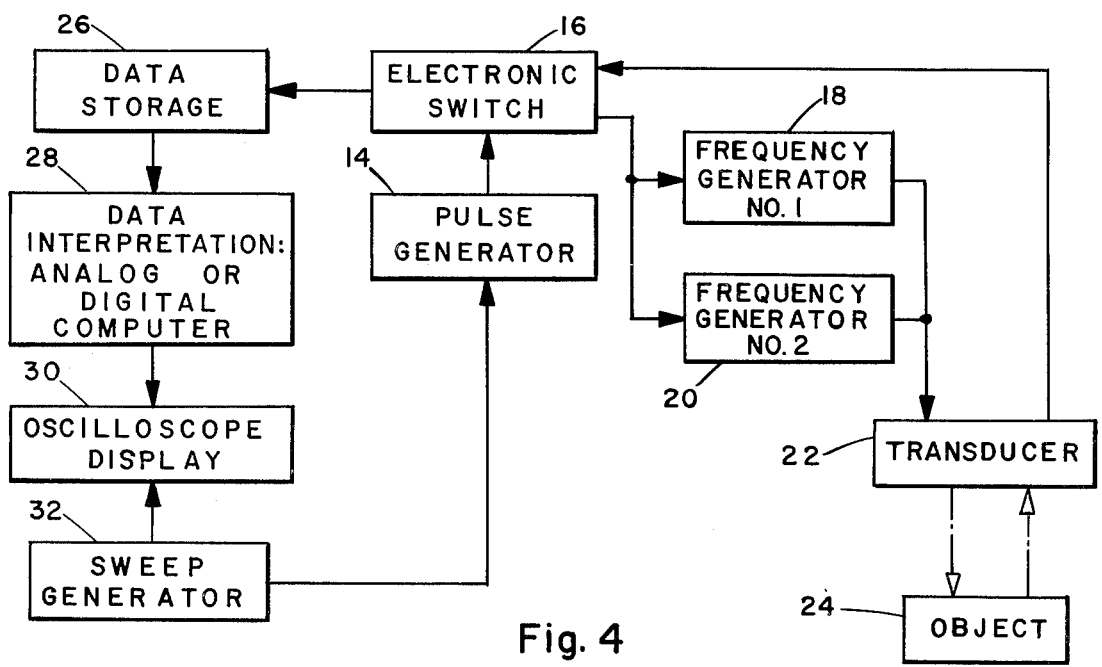
FIG. 4 is a schematic illustration of a preferred embodiment of the present invention.

The system of the present invention takes advantage of these features of scattered waves, and an exemplary system in accordance with the invention for utilizing such waves is schematically illustrated in FIG. 4. The system as best illustrated in FIG. 4 comprises in its simplest form a pulse generator 14 connected through a suitable electronic switching circuit 16 to two or more frequency generators 18 and 20. The frequency generators 18 and 20 are connected to a transducer 22 which is coupled to an object 24 such as a portion of a human body. The transducer 22 is connected through the electronic switch 16 to a data storage device 26 which in turn is connected to a data interpretation system 28 such as an analog or digital computer. The data interpretation system 28 is then connected to a suitable display device such as an oscilloscope or CRT 30 on which the interpretated data is displayed. A sweep generator 32 interconnected with the pulse generator is also connected to the oscilloscope 30. In the preferred embodiment the system includes multiple frequency generators such that pairs of ultrasonic waves may be generated and transmitted either alternately or simultaneously. These pair of waves, as will be pointed out later, enhances the image capabilities of the system. The construction of the equipment of the system of FIG. 4 is well within the state of the art having in mind the requirement of the present concept. In other words, having in mind the objective of the present concept. In other words, having in mind the objective of generating waves matched to the size of a particular object to be detected and pick-up means for picking up and displaying the results of the backscattered waves rather than the primarily reflected specular waves. The components are readily available off the shelf items, but must be put together in the unique cooperative arrangement as illustrated. Preferably the transducer 22 is a point source transducer having one common transmitting and receiving element. Switching from transmit to receiving mode is carried out by switch 16. Multiple transmitting and receiving transducers could be used if desired. In the system as illustrated, transmission would alternate with receiving, and would alternate between the two frequency generators 18 and 20.

Figure 5:
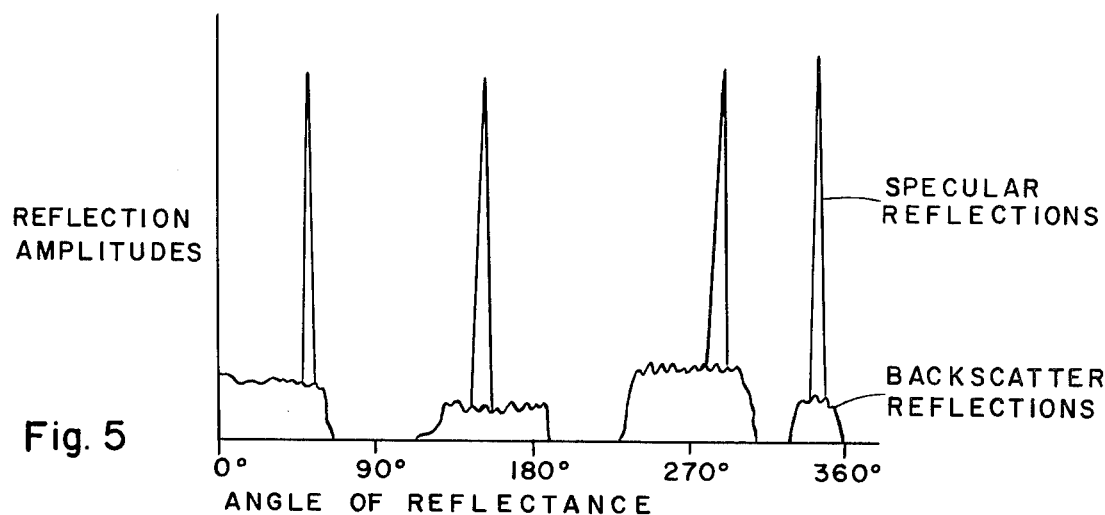
FIG. 5 is a graphic illustration of a comparison between the amplitude and angle of reflectance between specular and backscatter reflections.

The system in FIG. 4 shows, for illustrative purposes, the scanning of a portion of a human body such as the skull (not shown) having a foreign object 24, which might be for example, a projectile such as a bullet from a gun. A wave of specific frequency transmitted through the skull and reflecting from the object 24 would give a reflection amplitude illustrated, for example, in FIG. 5. The sharp peaks illustrate the amplitude and location of specular reflections. The amplitude and location of the scattered reflections are illustrated in the shorter more laterally extending wave patterns.

A better understanding of this comparison can be obtained from the following table of comparison:

Table 1

| ITEM | Specular vs Scattered Reflection; A comparison | |
|---|---|---|
| | SPECULAR REFLECTION | SCATTERING |
| Direction of returning wavefront | Obeys laws of reflection, angle of incidence = angle of reflection; Anisotropic. | Isotropic |
| Amplitude of returning wavefront | Independent of wavelength | Dependent on wavelength . (D/lambda) where . D = scattering cross- . section |
| Plotted amplitude vs direction for identical | | |

Table 1-continued

| | Specular vs Scattered Reflection; A comparison | |
|---|---|---|
| ITEM | SPECULAR REFLECTION | SCATTERING |
| objects: | | |
| In equation form | SR = f(A) | S = f(O, A, W1) |
| | where SR = specular reflection, S = scattered return = A, O = object size, A = amplitude of incident wavefront W = Wavelength (lambda) of incident wavefront | |
| Advantages | Relative ease of detection and display of reflected wavefront due to large amplitude. No linear translation of detector necessary. | May need only single point from which to . scan a sector |
| | | . Allows one . to "define" a range . of particular size of . particle or object . obtaining histologically . useful information as . a result. |
| Disadvantages | Requires long time for scan due to multiple positioning that must be used to completely delineate complex structures. Not characteristic for tissue type. | Requires somehwhat more sophisticated electronics due to the high gain differential amplifiers required. |

Figure 9:
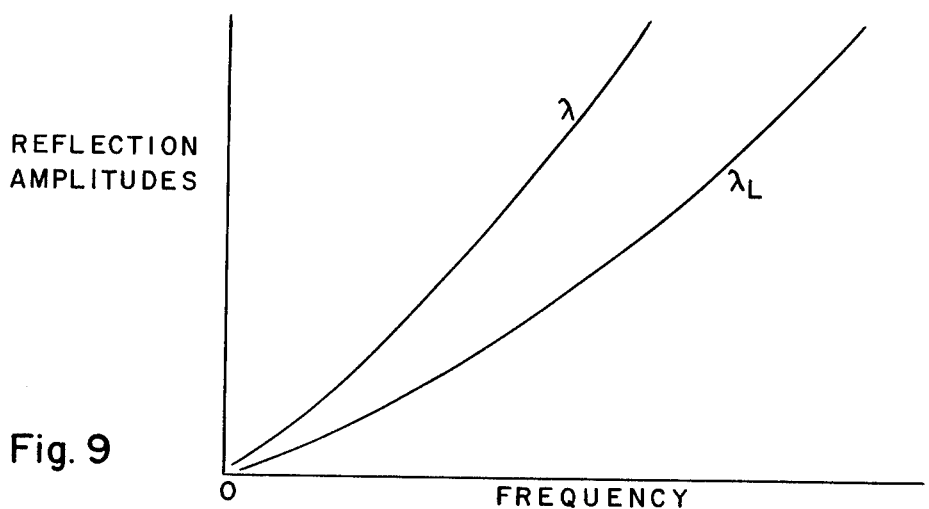
FIG. 9 is a graphic illustration of amplitude and frequency for a given wavelength.
Figure 10:
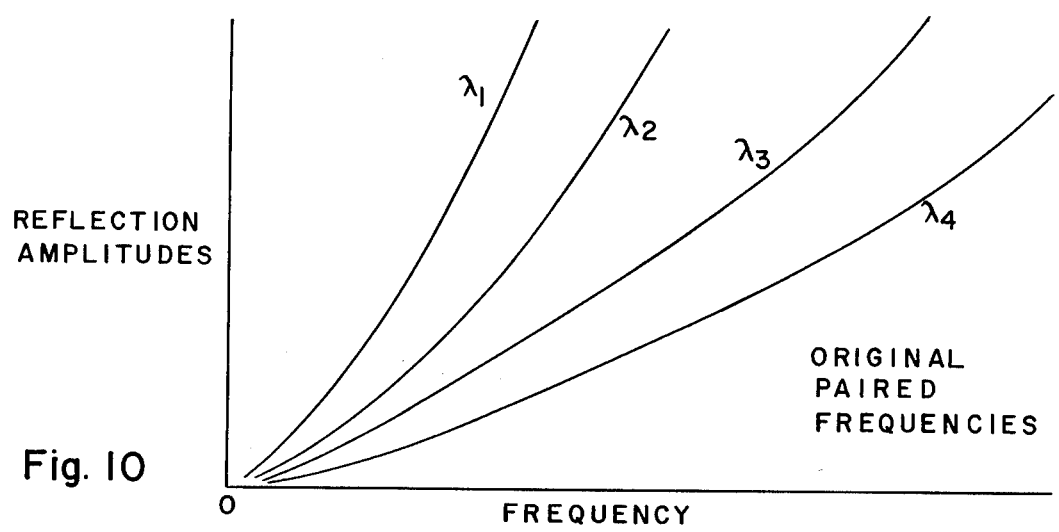
FIG. 10 is like FIG. 9 for additional wavelengths.
Figure 11:
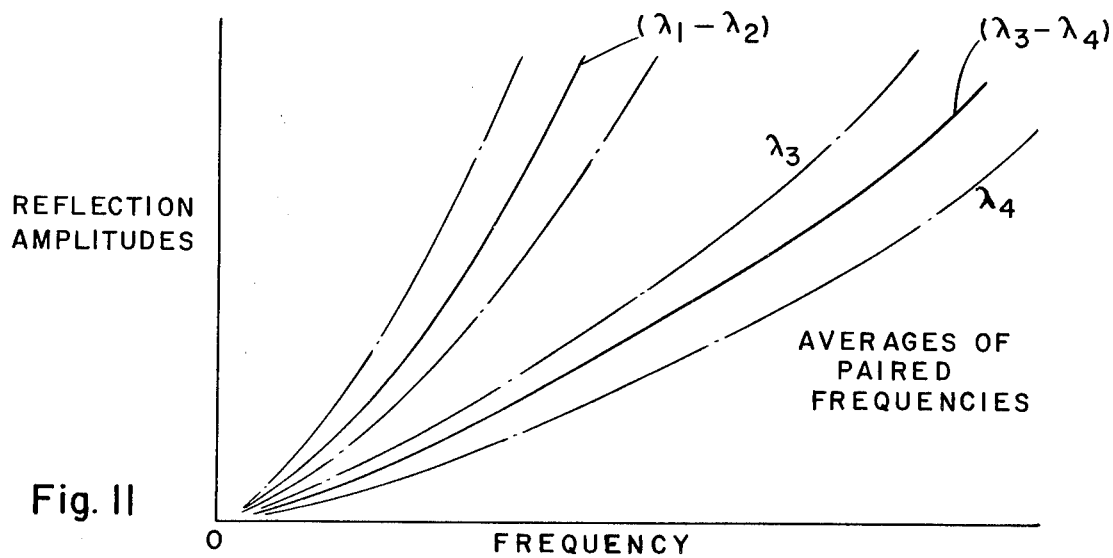
FIG. 11 is like FIG. 10 showing the averages of the frequencies of FIG. 10.

Returning to the basic principle of Rayleigh backscatter that the amplitude of scattering of the wave front is dependent upon the relationship between the wavelength of the incident wave and the reflecting object size, as illustration of which is shown in FIG. 9. In other words, as the wavelength of the incident wave front changes, the efficiency of reflection also changes. Specifically, if S=function of (O, lambda, A), it can be shown that by holding object size (O) and incident amplitude (A) constant and varying the wavelength, the amplitude of scattering (A) will change.

This difference in scattering efficiency between two wave fronts of different frequencies is the concept upon which this new ultrasound imaging technique is based.

Figure 6:
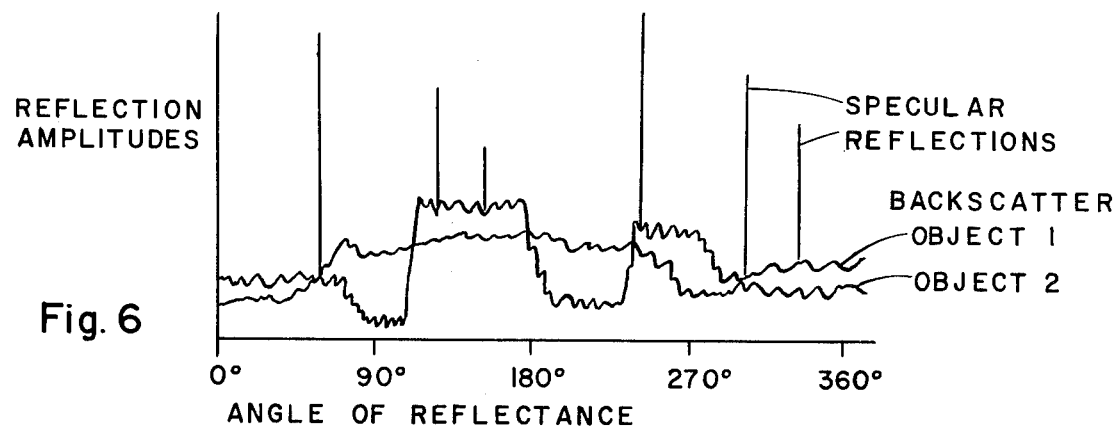
FIG. 6 is a graphic illustration like FIG. 5 from two objects.
Figure 7:
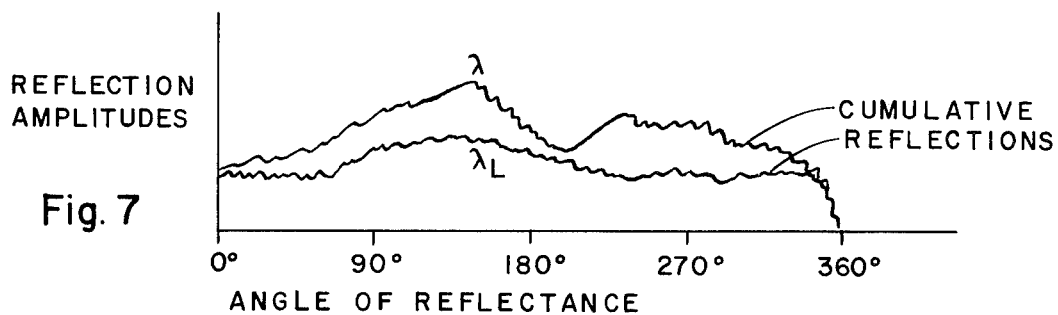
FIG. 7 is a graphic illustration of the cumulative reflections of the two waves of FIG. 6.
Figure 8:
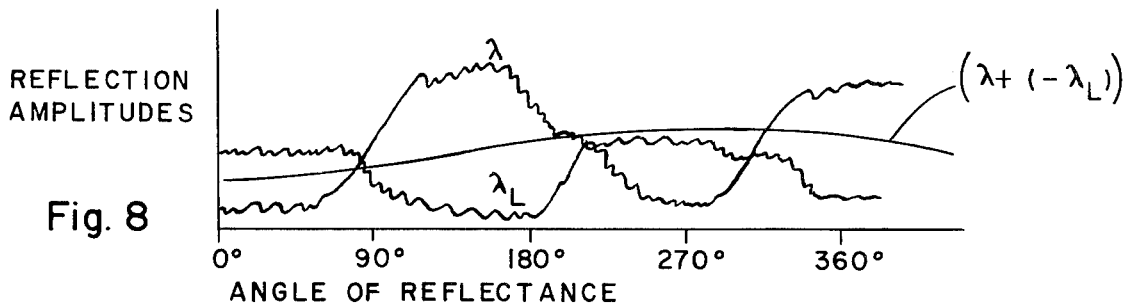
FIG. 8 is a graphic illustration like FIG. 7, with the additional illustration of differential of the curves.

If amplitude were plotted against frequency for two frequencies and evaluated for these two frequencies and differentially amplified we see the results we obtained from the plot in FIG. 6, the result in FIG. 7 with the specular reflections tending to completely cancel out leaving only the Rayleigh backscatter. Display of the information thus obtained yields an image which represents the size and configuration of the reflecting object.

Using Rayleigh backscatter and dual pairing of signals it should be possible to create visible contrast between regions having differeing scattering cross sections.

In order to further refine this system an internal referencing device can be provided by using a phantom containing regions of substances having known scattering cross-sections.

The system in essence provides pulse generating means for admitting at least two different frequencies of pulses with transducer means for directing the pulses in a beam or the like at or into an object with means for receiving reflected and scattered waves from the object. The transducer can serve as both the transmitter and receiver with electronic switching of the transducer between transmitting and receiving modes.

Thus, the system can alternate between transmission of a pulse and receiving of the reflection of that pulse, the transmission of a second frequency pulse and the receipt of that pulse and producing an echo signal or the like for storage in a data storage system as well as display on a display system, such as an oscillascope. In the present system the echo signals received from the object are differentially amplified in the data interpretation system, such as a computer, such that, for example, one echo is subtracted from the other, enhancing the difference between the Rayleigh backscatter waves received from the object. The specular reflections largely cancel out. The result of this process is to produce a signal defining the scattering characteristics of the object being studied. The resulting signals are then displayed on a screen, thus giving a visual indication of the internal characteristics of the body.

The method of the present invention includes the steps of alternately producing signals of different frequencies and receiving the alternate resulting echoes of reflections and processing the echos by substracting the one signal from the other and thereafter displaying the remaining differential signal to indicate a characteristic of the body or object being examined.

The system has the capability of producing multiple pairs of pulses of matched frequencies such that a wide range of frequencies can be selected for the examination of objects.

The analyzing and displaying of the data can be such that the display is an image representing the two or three-dimensional distribution of scattering cross-sections within the examined object.

A major advantage of the present system is the utilization of a point source of pulses of sonic waves with the transmitting and receiving transducer scanning a sector from a single point without linear translation while still producing a complete image of the object being examined.

While the present invention has been illustrated and described by means of specific embodiments, it is to be understood that numerous changes and modifications may be made therein without departing from the spirit and scope of the invention as defined in the appended claims.

Having described my invention, I now claim:

1. An ultrasonic imaging system comprising in combination:

ultrasonic generating means for generating at least a pair of pulses of slightly differing ultrasonic frequencies, means for transmitting said ultrasonic waves to an object;

means for individually detecting both frequencies scattered from said object, and means for differentially amplifying said scattered waves and displaying an image representative of the regional scattering cross-section of the interior of said object.

2. The system of claim 1, wherein said ultrasonic generating means includes means for generating paired pulses whose difference in frequency is chosen to optimize the measurement of the amplitude of scattering from said object.

3. The ultrasonic system of claim 2, wherein the wavelength of the waves transmitted to the object is large in relation to the size of the scattering sources within the object.

4. The ultrasonic imaging system of claim 2, wherein said means for matching the frequency of said ultrasonic waves to the size of the scattering source includes variable frequency generating means.

5. The ultrasonic imaging system of claim 4, wherein said variable frequency generating means includes at least a pair of variable frequency generators.

6. The imaging system of claim 1, wherein said system includes a single transducer for sending and receiving said pulses and at least a pair of distinct frequency generators.

7. The ultrasonic imaging system of claim 6, wherein said system includes electronic switching means for switching alternately between sending and receiving of said pulses.

8. The ultrasonic system of claim 7, wherein said system includes electronic switching means for switching alternately between the distinct frequency generators.

9. The system of claim 6, wherein each of said distinct frequency generators is variable in frequency.

10. The ultrasonic imaging system of claim 6, wherein each frequency generator is arranged to generate pairs of matched frequencies.

11. The ultrasonic imaging system of claim 10, wherein said means for analyzing said scattered waves includes data storage means.

12. The ultrasonic imaging system of claim 1, wherein said means for analyzing said scattered waves comprises an electronic means to subtract one of said waves from the other of said waves and generate a signal representative of the difference thereof.

13. The ultrasonic imaging system of claim 12, wherein said signal from said electronic means is displayed on an oscilloscope.

14. A method of ultrasonic imaging comprising the steps of:

generating and transmitting at least a pair of pulses of distinct ultrasonic frequencies to an object under examination, receiving and recording the amplitude of waves returned from said object, analyzing said waves by subtracting the amplitude of one of said waves from the amplitude of other of said waves, amplifying said difference, and displaying said differences between the amplitudes of said waves by visual means.

15. The method in accordance with claim 14, wherein said method includes the step of matching the frequency wavelengths of said pulses to the size of said scattering objects.

16. The method in accordance with claim 14, including the steps of alternately sending and receiving said alternate frequency pulses.

17. The method in accordance with claim 14, wherein said paired pulses are transmitted and received from a single pulse source.

18. The method in accordance with claim 14, including the step of determining an absolute scattering cross-section of a scattering object using a phantom reference having known scattering cross-section characteristics.

* * * * *